United States Patent
Schulze zur Wiesche et al.

(10) Patent No.: US 10,780,038 B2
(45) Date of Patent: Sep. 22, 2020

(54) HAIR TREATMENT AGENT CONTAINING AT LEAST ONE ACID PROTEIN AND AT LEAST ONE SALT

(71) Applicant: Henkel AG & Co. KGaA, Duesseldorf (DE)

(72) Inventors: Erik Schulze zur Wiesche, Hamburg (DE); René Krohn, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 52 days.

(21) Appl. No.: 15/535,482

(22) PCT Filed: Nov. 12, 2015

(86) PCT No.: PCT/EP2015/076436
§ 371 (c)(1),
(2) Date: Jun. 13, 2017

(87) PCT Pub. No.: WO2016/096267
PCT Pub. Date: Jun. 23, 2016

(65) Prior Publication Data
US 2017/0360674 A1    Dec. 21, 2017

(30) Foreign Application Priority Data
Dec. 17, 2014 (DE) .................. 10 2014 226 175

(51) Int. Cl.
*A61K 8/64* (2006.01)
*A61K 8/26* (2006.01)
*A61K 8/365* (2006.01)
*A61Q 5/00* (2006.01)
*A61Q 5/02* (2006.01)
*A61K 8/27* (2006.01)
*A61K 8/29* (2006.01)
*A61K 8/28* (2006.01)

(52) U.S. Cl.
CPC .......... *A61K 8/64* (2013.01); *A61K 8/26* (2013.01); *A61K 8/27* (2013.01); *A61K 8/28* (2013.01); *A61K 8/29* (2013.01); *A61K 8/365* (2013.01); *A61Q 5/004* (2013.01); *A61Q 5/02* (2013.01)

(58) Field of Classification Search
None
See application file for complete search history.

(56) References Cited

U.S. PATENT DOCUMENTS

| | | | | |
|---|---|---|---|---|
| 3,958,581 A | * | 5/1976 | Abegg | A61K 8/19 132/203 |
| 2003/0133896 A1 | | 7/2003 | Dietz et al. | |
| 2008/0279802 A1 | | 11/2008 | Muller et al. | |
| 2009/0068136 A1 | * | 3/2009 | Beumer | A61K 8/88 424/70.16 |
| 2014/0116458 A1 | * | 5/2014 | Krueger | A61Q 5/12 132/202 |
| 2014/0248229 A1 | * | 9/2014 | Krueger | A61Q 5/12 424/70.17 |

FOREIGN PATENT DOCUMENTS

| | | | |
|---|---|---|---|
| DE | 10051773 A1 | 4/2002 | |
| EP | 0186025 B1 * | 6/1991 | ............ A61K 8/645 |
| EP | 1676604 A1 | 7/2006 | |
| WO | 2009106399 A1 | 9/2009 | |

OTHER PUBLICATIONS

"Hydrolyzed Collagen" Wikipedia <https://en.wikipedia.org/wiki/Hydrolyzed_collagen> , accessed Jun. 22, 2018. (Year: 2018).*
Ansmann, English translation of EP 0186025 B1 (Year: 1991).*
Maria Fernanda Reis Gavazzoni Dias, Andréia Munck de Almeida, Patricia Makino Rezende Cecato, Andre Ricardo Adriano, and Janine Pichler "The Shampoo pH can Affect the Hair: Myth or Reality?" Int J Trichology. Jul.-Sep. 2014; 6(3): 95-99 (Year: 2014).*
EPO, International Search Report and Written Opinion issued in International Application No. PCT/EP2015/076436, dated Jan. 22, 2016.
Andrews, P., "Estimation of the Molecular Weights of Proteins by Sephadex Gel-Filtration", Biochem. J., 1964, 91, pp. 222-233.
Anonymous, "GNPD—Shampoo", Jun. 2007.
Cohen, Steven A., "Quantitation of Amino Acids and Amines by Chromatography: Methods and Protocols", Journal of Chromatography Library, vol. 70, Elsevier, 2005, pp. 242-267.
Kuiken, K. A. et al., "Essential Amino Acid Composition of Soy Bean Meals Prepared from Twenty Strains of Soy Beans", J. Biol. Chem., Jan. 1948, pp. 29-36.
Pomeranz, Y. et al., "Protein Content and Amino Acid Composition of Oat Species and Tissues", Jan. 1973, pp. 702-707.
Woychik, J. H. et al., "Wheat Gluten Proteins: Amino Acid Composition of Proteins in Wheat Gluten", Jul. 1961, pp. 307-310.

* cited by examiner

*Primary Examiner* — Nicole P Babson
(74) *Attorney, Agent, or Firm* — Lorenz & Kopf, LLP

(57) ABSTRACT

A cosmetic agent for treating keratin fibers is provided herein. The cosmetic agent includes, in a cosmetically acceptable carrier, in relation to the total weight of the cosmetic agent, from about 0.001 to about 10 wt. % of at least one protein which has a content of glutamic acid and/or aspartic acid of from about 10 to about 60%, in relation to the total content of all amino acids of the protein. The cosmetic agent further includes, in a cosmetically acceptable carrier, in relation to the total weight of the cosmetic agent, from about 0.01 to about 10 wt. % of at least one salt which includes at least one divalent cation, and/or of at least one salt which includes at least one trivalent cation.

20 Claims, No Drawings

HAIR TREATMENT AGENT CONTAINING AT LEAST ONE ACID PROTEIN AND AT LEAST ONE SALT

CROSS-REFERENCE TO RELATED APPLICATION

This application is a U.S. National-Stage entry under 35 U.S.C. § 371 based on International Application No. PCT/EP2015/076436, filed Nov. 12, 2015 which was published under PCT Article 21(2) and which claims priority to German Application No. 102014226175.9, filed Dec. 17, 2014, which are all hereby incorporated in their entirety by reference.

TECHNICAL FIELD

The present disclosure lies in the field of cosmetics and relates to a cosmetic agent which contains at least one acid protein and at least one salt comprising at least one divalent cation and/or at least one salt comprising at least one trivalent cation. The present disclosure also relates to a method for maintaining the color of dyed keratin fibers with use of the cosmetic agent as contemplated herein. Lastly, the present disclosure relates to the use of a combination of at least one acid protein and at least one salt containing at least one divalent cation and/or at least one salt containing at least one trivalent cation, for retaining the color of dyed keratin fibers.

BACKGROUND

Changing the shape and the color of hair is an important area of modern cosmetics. The appearance of the hair can thus be adapted both to the current fashion trends and to the individual wishes of the consumer in question. The trendy coloring of hairstyles or the coating of grey or white hair with fashionable or natural tones is usually performed with color-changing agents, which dye the hair permanently or only momentarily, i.e. temporarily.

For permanent, intense coloring with corresponding fastness properties, what are known as oxidation dyes are used. Such colorants usually contain oxidation dye precursors, or what are known as developer components and coupler components. The developer components form the actual dyes with one another or with coupling to one or more coupler components, under the influence of oxidizing agents or atmospheric oxygen. The oxidation dyes are characterized by excellent, long-lasting coloring results.

For temporary coloring, colorants or tints which contain what are known as direct dyes as coloring component are usually used. These direct dyes are dye molecules which are drawn directly onto the substrate and which do not require an oxidative process in order to develop the color. These dyes include, by way of example, henna, which is already known from ancient times for coloring the body and hair. In contrast to the coloring obtainable using oxidation dyes, the coloring results of temporary coloring appear to last for a shorter period of time.

The keratin fibers, in particular hair, dyed by employing the previously described dyeing systems, however, have the disadvantage that they can change undesirably under external influences—for example during or after cleaning of the hair.

An "undesirable change" is understood to mean fading or bleeding, the loss of color brilliance, and a shift in color of the tone of the hair attained by the coloring process in question. An undesirable change to the hair color generally occurs during or after cleaning of the hair. The contact of the hair with water and surfactants, but also the massaging-in of the shampoo, the towel-drying of the hair once the shampoo has been rinsed out, or the heat from a hairdryer during a subsequent drying process can impair the adhesion of the hair dye and can lead to an undesirable change in color and/or to less brilliance of the hair color. The resultant undesirable change is additionally intensified by further ambient influences and/or the effects of the sun.

Hair treatment agents which avoid the undesirable change to dyed hair and which maintain the color of the dyed hair are described by way of example in the laid-open application EP 1 676 604 A1 and contain, besides an anionic surfactant and a specific silicone, also at least one water-soluble salt, preferably sodium sulfate.

The hair treatment agents known in the prior art, however, do not always lead to the desired maintenance of color, in particular a reduction of the color shift.

BRIEF SUMMARY

A cosmetic agent for treating keratin fibers is provided herein. The cosmetic agent includes, in a cosmetically acceptable carrier, in relation to the total weight of the cosmetic agent, from about 0.001 to about 10 wt. % of at least one protein which has a content of glutamic acid and/or aspartic acid of from about 10 to about 60%, in relation to the total content of all amino acids of the protein. The cosmetic agent further includes, in a cosmetically acceptable carrier, in relation to the total weight of the cosmetic agent, from about 0.01 to about 10 wt. % of at least one salt which includes at least one divalent cation, and/or of at least one salt which includes at least one trivalent cation.

Another cosmetic agent for treating keratin fibers is also provided herein. The agent includes, in a cosmetically acceptable carrier, in relation to the total weight of the cosmetic agent from about 0.001 to about 10 wt. % of at least one protein which has a content of glutamic acid and/or aspartic acid of from about 10 to about 60%, in relation to the total content of all amino acids of the protein. The agent also includes, in a cosmetically acceptable carrier, in relation to the total weight of the cosmetic agent from about 0.01 to about 10 wt. % of at least one salt which includes calcium lactate and/or aluminum salts of formula $MAl(SO_4)_2$, in which M stands for a potassium ion. The agent further includes, in a cosmetically acceptable carrier, in relation to the total weight of the cosmetic agent from about 0.01 to about 3 wt. % of at least one cationic polymer which includes a cationic polysaccharide. The cosmetic agent has a pH value, measured at 20° C., of from about pH 4.0 to about pH 5.0.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide a cosmetic agent for treating keratin fibers which avoids or at least mitigates the disadvantages of the prior art and which leads to an improved maintenance of color, in particular to a reduced color shift. Besides the improved maintenance of color, the cosmetic agents should have a good cleansing and/or nourishing performance and a high storage stability.

It has now surprisingly been found that the use of specific acid proteins in combination with at least one salt in cosmetic agents for treating hair leads to an improved maintenance of color. In particular, the undesirable shift or change in the hair color in the direction of yellow or blue can be avoided or reduced by the use as contemplated herein of the aforementioned combination. In addition, the use of the acid protein in combination with the at least one salt does not lead to unfavorable interactions with further ingredients of the cosmetic agents, such that a negative influence on the cleansing and/or nourishing performance and also the storage stability of these agents is avoided.

A first subject of the invention is therefore a cosmetic agent for treating keratin fibers, containing in a cosmetically acceptable carrier—in relation to the total weight of the cosmetic agent a) from about 0.001 to about 10 wt. % of at least one protein which has a content of glutamic acid and/or aspartic acid of from about 10 to about 60%, in relation to the total content of all amino acids of the protein, and b) from about 0.01 to about 10 wt. % of at least one salt which comprises at least one divalent cation, and/or of at least one salt which comprises at least one trivalent cation.

The term "keratin fibers" is understood as contemplated herein to mean furs, wool, feathers and human hair. Within the scope of the present disclosure it is particularly preferred if the cosmetic agents are used for the treatment of human hair.

Furthermore, the term "protein" within the scope as contemplated herein is understood to mean chemical compounds which, by employing peptide bonds, form condensation products of amino acids linked in an acid amide-like manner. The number of amino acids in the protein is preferably at least 2 and at most 1,000 amino acids. The term "protein" is understood as contemplated herein to also mean hydrolysates of a protein which contain protein fractions having different amino acid sequences and molecular weights.

In addition, the term "divalent cations" is understood within the scope of the present disclosure to mean cations which are twice positively charged. By contrast, the term "trivalent cations" is understood to mean cations which are thrice positively charged.

In addition, the term "cosmetic agents for treating keratin fibers" is understood preferably to mean hair cleansing agents such as shampoos, hair nourishing agents such as hair masks, rinses or nourishing hair sprays, and hairstyling agents such as hair gels, hairsprays or hair waxes.

Furthermore, the term "fatty alcohols" within the scope of the is understood to mean aliphatic, long-chain, monovalent, primary alcohols which comprise unbranched hydrocarbon groups having from about 6 to about 30 carbon atoms. The hydrocarbon groups can be saturated, but can also be mono- or polyunsaturated.

Lastly, the term "fatty acids" within the scope of the present disclosure is understood to mean aliphatic monocarboxylic acids with unbranched carbon chain which comprise hydrocarbon groups having from about 6 to about 30 carbon atoms. The hydrocarbon groups can be either saturated also mono- or polyunsaturated.

The value of the total amount with regard to the components of the cosmetic agent relates in the present case—unless specified otherwise—to the total amount of active substance of the component in question.

The cosmetic agents as contemplated herein contain a cosmetic carrier. As contemplated herein, the cosmetic carrier is preferably aqueous, alcoholic or aqueous-alcoholic. Within the scope of the present disclosure, creams, emulsions, gels or surfactant-containing foaming solutions, such as shampoos, mousse aerosols, or other preparations suitable for application to the hair, can be used by way of example.

An aqueous carrier as contemplated herein contains at least about 30 wt. %, in particular at least about 50 wt. % of water, in relation to the total weight of the cosmetic agent.

The term aqueous-alcoholic carriers within the sense of the present disclosure is understood to mean water-containing compositions containing a $C_1$-$C_4$ alcohol in a total amount of from about 3 to about 90 wt. %, in relation to the total weight of the cosmetic agent, in particular ethanol or isopropanol.

The cosmetic agents as contemplated herein can additionally contain further organic solvents, such as methoxybutanol, ethyldiglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred here, wherein the solvent is contained in a total amount of from about 0.1 to about 30 wt. %, preferably from about 1 to about 20 wt. %, in particular from about 2 to about 10 wt. %, in relation to the total weight of the cosmetic agent.

The cosmetic agent as contemplated herein contains, as first essential constituent a), at least one protein which contains a specific proportion of acidic amino acids, in particular glutamic acid and/or aspartic acid.

As contemplated herein, the at least one protein preferably has a content of glutamic acid and/or aspartic acid of from about 20 to about 60%, preferably from about 30 to about 60%, in particular from about 40 to about 60%, in relation to the total content of all amino acids of the protein. The content of glutamic acid and/or aspartic acid in the protein used as contemplated herein relates to the proportion, as a percentage, of the aforementioned amino acids in the total content, in particular the total amount, of all amino acids occurring in the protein. The content of glutamic acid and/or aspartic acid can be determined by way of example by hydrolysis of the protein, subsequent derivatization of the amino acids, and subsequent determination of the derivatized amino acids by employing HPLC (S. A. Cohen in "Quantification of amino acids and amines by chromatography—methods and protocols", Elsevier B.V., 2005, pages 242 to 267). Proteins which comprise the aforementioned content of acidic amino acids lead, in combination with the at least one salt, to a particularly good maintenance of color or to a particularly strong reduction of the color shift of dyed keratin fibers, in particular hair.

In accordance with a further preferred embodiment, the at least one protein has a $pK_s$ value of from about 3.5 to about 6.5, preferentially from about 4.0 to about 6.0, preferably from about 4.5 to about 6.0, in particular from about 4.5 to about 5.5. The aforementioned $pK_s$ values can be determined by way of example by employing an acid-based titration with use of indicators known to a person skilled in the art and determination of the pH value at the half equivalence point. At this point, the acid and its corresponding base are present at the same concentration, and the $pK_s$ value corresponds to the pH value. The use of acid proteins which have the above $pK_s$ values in combination with the at least one salt provides particularly good results in respect of the maintenance of the color of dyed keratin fibers.

On account of the high total content of acidic amino acids, the protein used in the cosmetic agents as contemplated herein has an acidic pH value. It is therefore preferred if a 1 wt. % solution of the at least one protein, in relation to the total weight of the solution, has a pH value, measured at 20° C., of from about pH 3.5 to about pH 7.0, preferably from about pH 3.5 to about pH 6.0, in particular from about pH 3.5 to about pH 5.2. A solution of the at least one protein is understood within the scope of the present disclosure to mean a solution in which 1 wt. % of the protein is fully dissolved in a solvent, preferably water.

Particularly good results with regard to the maintenance of color, the cleansing and/or nourishing performance and also the storage stability of the cosmetic agents as contemplated herein are obtained if the at least one protein has a mean molecular weight $M_w$ of from about 100 to about 5,000 Da, preferentially from about 100 to about 4,000 Da, preferably from about 200 to about 3,000 Da, in particular from about 300 to about 1,200 Da. The mean molecular weight $M_w$ can be determined for example by gel permeation chromatography (GPC) (Andrews P.; "Estimation of the Molecular Weights of Proteins by Sephadex Gel-Filtration"; Biochem. J., 1964, 91, pages 222 to 233). The use of acid proteins which contain the aforementioned mean molecular weights $M_w$ leads on the one hand to an excellent color protection with simultaneously high cleansing and/or nourishing performance and storage stability.

The at least one protein preferably contains from about 2 to about 40 amino acids, preferentially from about 2 to about 30 amino acids, preferably from about 2 to about 25 amino acids, in particular from about 2 to about 18 amino acids. Proteins which comprise the aforementioned number of amino acids have proven to be particularly advantageous within the scope of the present disclosure with regard to the maintenance of color and the cleansing and/or nourishing performance.

As contemplated herein, the at least one protein is preferably contained in a total amount of from about 0.001 to about 8 wt. %, preferentially from about 0.01 to about 5 wt. %, preferably from about 0.1 to about 3 wt. %, in particular from about 0.3 to about 2 wt. %, in relation to the total weight of the cosmetic agent. The use of the aforementioned amounts of the at least one acid protein in the cosmetic agents as contemplated herein on the one hand ensures an excellent maintenance of the color of the dyed keratin fibers and on the other hand does not lead to negative interactions with further ingredients of the cosmetic agents as contemplated herein, such that a satisfactory cleansing and/or nourishing performance and a high storage stability of these agents results.

As second essential component b), the cosmetic agents as contemplated herein contain at least one salt. Within the scope of the present disclosure, salts are understood to mean chemical compounds which are constructed from positively charged ions (what are known as cations) and negatively charged ions (what are known as anions). These include both inorganic salts, in which neither the anions nor the cations are organic compounds, i.e. compounds based on carbon, and also organic salts, in which at least one anion or one cation is present in the form of an organic compound.

Particularly good effects with regard to the color protection, the cleansing and/or nourishing performance, and also the storage stability of the cosmetic agents as contemplated herein are obtained if a salt of lactic acid, selected from the group of magnesium salts, calcium salts, copper salts, zinc salts, iron(II) salts and mixtures of these salts, in particular calcium salts of lactic acid, is contained as salt comprising at least one divalent cation. Within the scope of the present disclosure, the use of calcium salts of lactic acid, also referred to as calcium lactate, is particularly preferred. Calcium lactate leads, in conjunction with the at least one acid protein, to a particularly good color protection and also a particularly high reduction of the color shift of dyed keratin fibers. In addition, the use of the aforementioned salts does not lead to a negative influence on the cleansing and/or nourishing performance of the cosmetic agents as contemplated herein.

The salt which comprises at least one divalent cation is preferably contained in a total amount of from about 0.01 to about 8 wt. %, preferentially from about 0.1 to about 5 wt. %, preferably from about 0.2 to about 3 wt. %, in particular from about 0.3 to about 2 wt. %, in relation to the total weight of the cosmetic agent. The use of the at least one salt, preferably calcium lactate, in the aforementioned amounts results in a particularly good color protection and does not lead to a precipitation of the acid protein or to negative interactions with further conventional ingredients of the cosmetic agent as contemplated herein, such that a high storage stability is ensured. In addition, the use of these salt amounts also does not lead to a negative influence on the cleansing and/or nourishing performance of the cosmetic agents as contemplated herein.

In addition to or instead of the salt comprising at least one divalent cation, a salt which comprises at least one trivalent cation can be used within the scope of the present disclosure. It is therefore preferred within the scope of an embodiment of the present disclosure if a salt from the group of titanium salts, zirconium salts, gallium salts, aluminum salts, in particular aluminum salts of formula $MAl(SO_4)_2$, in which M stands for a potassium, sodium, guanidinium or ammonium ion, is contained as salt comprising at least one trivalent cation. Within the scope of the present disclosure, the use of aluminum salts, in particular those of the above formula $MAl(SO_4)_2$ with $M=K^+$, which are referred to as what are known as alums, is particularly preferred. The use of alums leads, in combination with the acid protein and where applicable with the further salt, in particular calcium lactate, to particularly good results with regard to the maintenance of color and the storage stability of the cosmetic agents as contemplated herein.

Within the scope of the present disclosure it is preferred if the salt comprising at least one trivalent cation is used in a specific total amount in the cosmetic agents as contemplated herein. Cosmetic agents that are preferred as contemplated herein are therefore characterized in that the salt comprising at least one trivalent cation is contained in a total amount of from about 0.01 to about 5 wt. %, preferentially from about 0.05 to about 4.5 wt. %, preferably from about 0.1 to about 4.0 wt. %, more preferably from about 0.15 to about 3.5 wt. %, even more preferably from about 0.5 to about 3.0 wt. %, in particular from about 0.8 to about 2.5 wt. %, in relation to the total weight of the cosmetic agent. The use of the at least one salt, preferably an aluminum salt of formula $MAl(SO_4)_2$ with $M=K^+$, in the aforementioned amounts results in a particularly good color protection and does not lead to a precipitation of the acid protein or to negative interactions with further conventional ingredients of the cosmetic agent as contemplated herein, such that a high storage stability is ensured. In addition, the use of these salt amounts also does not lead to a negative influence on the cleansing and/or nourishing performance of the cosmetic agents as contemplated herein.

Chelating and/or complexing agents, in particular nitrogen-containing chelating and/or complexing agents can have a negative effect on the salts necessarily contained in the cosmetic agents as contemplated herein in that they complex the cations of the partially to fully dissolved salts and thus impair the efficacy thereof. The cosmetic agents as contemplated herein are therefore preferably substantially free from nitrogen-containing chelating and/or complexing agents, such as β-alanine diacetic acid, diethylenetriamine pentamethylene phosphonic acid, sodium, potassium, calcium disodium, ammonium and triethanolamine salts of ethylenediaminetetraacetic acid (EDTA), hydroxyethyl ethylenediaminetetraacetic acid (HEDTA) and sodium salts thereof, sodium salts of nitrilotriacetic acid (NTA), diethylenetriaminepentaacetic acid, pentasodium amino trimethylene phosphonate, pentasodium ethylenediamine tetramethylene phosphonate, pentasodium diethylenetriaminepentaacetate, tetra hydroxyethyl ethylenediamine, tetra hydroxypropyl ethylenediamine, trisodium ethylenediamine disuccinate, tetrasodium-N,N-bis (carboxymethyl)glutamate and tetrasodium DL-alanine-N, N-diacetate.

The term "substantially free" is understood as contemplated herein to mean that the cosmetic agents contain at most about 0.01 wt. %, preferably at most about 0.005 wt. %, in particular at most about 0.001 wt. %, in relation to the total weight of the cosmetic agent, of nitrogen-containing chelating and/or complexing agents.

It has been found that the maintenance of the color of dyed keratin fibers is particularly high after a number of cleaning processes if the cosmetic agents as contemplated herein have a specific pH value. Within the scope of the present disclosure it is therefore preferred if the cosmetic agent has a pH value, measured at 20° C., of from about pH 4.0 to about pH 5.0, preferentially from about pH 4.1 to about pH 4.9, preferably from about pH 4.2 to about pH 4.8, in particular from about pH 4.3 to about pH 4.7.

In a preferred embodiment the cosmetic agents as contemplated herein are characterized in that they contain—in relation to the total weight of the cosmetic agents as contemplated herein from about 0.001 to about 10 wt. % of at least one protein which has a content of glutamic acid and/or aspartic acid of from about 10 to about 60%, preferentially from about 20 to about 60%, preferably from about 30 to about 60%, in particular from about 40 to about 60% in relation to the total content of all amino acids of the protein, and from about 0.01 to about 10 wt. %, preferentially about 0.01 to about 8 wt. %, preferably from about 0.1 to about 5 wt. %, more preferably from about 0.2 to about 3 wt. %, in particular from about 0.3 to about 2 wt. % of calcium lactate, wherein the cosmetic agent has a pH value, measured at 20° C., of from about pH 4.0 to about pH 5.0, preferentially from about pH 4.1 to about pH 4.9, preferably from about pH 4.2 to about pH 4.8, in particular from about pH 4.3 to about pH 4.7.

In a further preferred embodiment the cosmetic agents as contemplated herein are characterised in that they contain— in relation to the total weight of the cosmetic agents as contemplated herein from about 0.001 to about 10 wt. % of at least one protein which has a content of glutamic acid and/or aspartic acid of from about 10 to about 60%, preferentially from about 20 to about 60%, preferably from about 30 to about 60%, in particular from about 40 to about 60% in relation to the total content of all amino acids of the protein, and from about 0.01 to about 10 wt. %, preferentially from about 0.01 to about 5 wt. %, preferably from about 0.05 to about 4.5 wt. %, more preferably from about 0.1 to about 4.0 wt. %, even more preferably from about 0.15 to about 3.5 wt. %, in particular from about 0.8 to about 2.5 wt. % of aluminum salts of formula $MAl(SO_4)_2$, in which M stands for a potassium ion, wherein the cosmetic agent has a pH value, measured at 20° C., of from about pH 4.0 to about pH 5.0, preferentially from about pH 4.1 to about pH 4.9, preferably from about pH 4.2 to about pH 4.8, in particular from about pH 4.3 to about pH 4.7.

In yet a further preferred embodiment the cosmetic agents as contemplated herein are characterised in that they contain—in relation to the total weight of the cosmetic agents as contemplated herein from about 0.001 to about 10 wt. % of at least one protein which has a content of glutamic acid and/or aspartic acid of from about 10 to about 60%, preferentially from about 20 to about 60%, preferably from about 30 to about 60%, in particular from about 40 to about 60% in relation to the total content of all amino acids of the protein, and calcium lactate and aluminum salts of formula $MAl(SO_4)_2$, in which M stands for a potassium ion, in a total amount of from about 0.01 to about 10 wt. %, wherein the cosmetic agent has a pH value, measured at 20° C., of from about pH 4.0 to about pH 5.0, preferably from about pH 4.1 to about pH 4.9, preferably from about pH 4.2 to about pH 4.8, in particular from about pH 4.3 to about pH 4.7.

The cosmetic agents as contemplated herein can contain further active substances and ingredients conventional for hair treatment agents.

The cosmetic agents as contemplated herein preferably contain at least one surfactant. In accordance with an embodiment of the present disclosure it is therefore preferred if the cosmetic agent additionally contains at least one surfactant selected from the group of anionic surfactants, cationic surfactants, amphoteric surfactants, non-ionic surfactants, and mixtures thereof, in a total amount of from about 0.01 to about 20 wt. %, in relation to the total weight of the cosmetic agent.

Anionic surfactants are preferred in particular when the cosmetic agent as contemplated herein is present in the form of a hair shampoo. All anionic surfactants or surface-active substances suitable for use on the human body can be used as anionic surfactants in the cosmetic agents as contemplated herein. These are characterized by a hydrophilic anionic group, such as a carboxylate, sulfate, sulfonate or phosphate group and a lipophilic group having approximately 8 to 30 carbon atoms. These surfactants can additionally comprise glycol or polyglycol ether groups, ester, ether and amide groups, and hydroxyl groups. The group of anionic surfactants that can be used within the scope of the present disclosure includes, for example:

ether carboxylic acids of formula $R-O-(CH_2-CH_2O)_x-CH_2-COOH$, in which R is a linear or branched, saturated or unsaturated alkyl group having 8 to 30 carbon atoms and x=0 or is 1 to 16, acyl glutamates and/or (acyl)isethionates having 8 to 24 carbon atoms in acyl group, sulfosuccinic acid mono- and/or dialkyl esters having 8 to 24 carbon atoms in the alkyl group and sulfosuccinic acid monoalkyl polyoxyethyl esters having 8 to 24 carbon atoms in the alkyl group and 1 to 6 oxyethyl groups, and/or alkyl sulfate and/or alkyl polyglycol ether sulfate salts of the formula (I) $R^1-(OCH_2-CH_2)_x-OSO_3^-X^+$, in which $R^1$ preferably stands for a linear or branched, saturated or unsaturated alkyl group having 8 to 30 carbon atoms, x stands for the number 0 or 1 to 12, and X stands for an alkali, alkaline earth, ammonium, or alkanolamine ion.

Particularly preferred anionic surfactants are straight-chained or branched alkyl ether sulfates of the aforementioned formula (I) which contain an alkyl group having 8 to 18, in particular having 10 to 16 carbon atoms, and 1 to 6 and in particular 2 to 4 ethylene oxide units. The sodium, magnesium and/or triethanolamine salts of linear or branched lauryl, tridecyl and/or myristyl sulfates which have a degree of ethoxylation of from 2 to 4 are preferred in particular.

The anionic surfactants are preferably used in specific total amounts. Preferred cosmetic agents as contemplated herein are therefore characterised in that they contain at least one anionic surfactant in a total amount of from about 0.1 to about 20 wt. %, in relation to the total weight of the cosmetic agent.

In this context, cosmetic agents as contemplated herein which are preferred are those which contain—in relation to the total weight of the cosmetic agents as contemplated herein from about 0.001 to about 10 wt. % of at least one protein which has a content of glutamic acid and/or aspartic acid of from about 10 to about 60%, preferentially from about 20 to about 60%, preferably from about 30 to about 60%, in particular from about 40 to about 60% in relation to the total content of all amino acids of the protein, calcium lactate and/or aluminum salts of formula MAl $(SO4)_2$, in which M stands for a potassium ion, in a total amount of from about 0.01 to about 10 wt. %, and from about 0.1 to about 20 wt. % of at least one anionic surfactant, selected from the group of alkyl sulfate and/or alkyl polyglycol ether sulfate salts of the formula (I) $R^1—(OCH_2—CH_2)_x—OS_3^-X^+$, in which $R^1$ preferably stands for a linear or branched, saturated or unsaturated alkyl group having 8 to 30 carbon atoms, x stands for the number 0 or 1 to 12, and X stands for an alkali, alkaline earth, ammonium, or alkanolamine ion, wherein the cosmetic agent has a pH value, measured at 20° C., of from about pH 4.0 to about pH 5.0, preferentially from about pH 4.1 to about pH 4.9, preferably from about pH 4.2 to about pH 4.8, in particular from about pH 4.3 to about pH 4.7.

If the cosmetic agents as contemplated herein are produced in the form of a nourishing rinse, the use of cationic surfactants is preferred. In this context, suitable cationic surfactants are quaternary ammonium compounds, esterquats and/or amidoamines, for example.

Preferred quaternary ammonium compounds are ammonium halides, in particular chlorides and bromides, such as alkyltrimethylammonium chlorides, dialkyldimethylammonium chlorides, and trialkylmethylammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride and the imidazolium compounds known under the INCI names Quaternium-27, Quaternium-83 and Quaternium-87. The alkyl chains of the above-mentioned surfactants preferably have 10 to 18 carbon atoms.

Esterquats are substances which contain both at least one ester function and at least one quaternary ammonium group as structural element. Preferred esterquats are quaternized ester salts of fatty acids with triethanolamine, quaternized ester salts of fatty acids with diethanol alkyl amines, and quaternized ester salts of fatty acids with 1,2-dihydroxypropyl dialkyl amines. Such products are sold for example under the trade names Stepantex®, Dehyquart®, Armocare® and Quartamin®.

The alkyl amido amines are usually produced by amidation of natural or synthetic fatty acids and fatty acid cuts with dialkylamino amines. A particularly suitable compound from this substance group is the stearamidopropyl dimethylamine commercially obtainable under the name Tegoamid® S 18.

The cationic surfactants are preferably used in specific total amounts. Preferred cosmetic agents as contemplated herein are therefore characterised in that they contain at least one cationic surfactant in a total amount of from about 0.1 to about 10 wt. %, in relation to the total weight of the cosmetic agent.

Surface-active compounds which comprise at least one quaternary ammonium group and at least one $—COO^{(-)}$ or $—SO_3^{(-)}$ group are referred to as amphoteric surfactants. Particularly suitable zwitterionic surfactants are what are known as the betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines having in each case 8 to 18 C atoms in the alkyl or acyl group, and cocoacylaminoethyl hydroxyethyl carboxymethyl glycinate. Particularly preferred amphoteric surfactants as contemplated herein are the carboxylic acid amide derivative known under the INCI name Cocamidopropyl Betaine and alkyl betaines having 10 to 20 carbon atoms in the alkyl group.

The non-ionic surfactants that can be used within the scope of the present disclosure comprise, as hydrophilic group, for example a polyol group, a polylalkylene glycol ether group, or a combination of polyol and polyglycol ether group. The non-ionic surfactants/emulsifiers that are suitable as contemplated herein preferably include $C_8$-$C_{30}$ fatty acid mono- and diesters of addition products of from 1 to 30 mol ethylene oxide with glycerol, amine oxides, addition products of from about 2 to about 50 mol ethylene oxide and/or 0 to about 5 mol propylene oxide with linear and branched fatty alcohols having 8 to 30 C atoms, with fatty acids having 8 to 30 C atoms, and with alkylphenols having 8 to 15 C atoms in the alkyl group, sorbitol fatty acid esters and addition products of ethylene oxide with sorbitol fatty acid esters, such as polysorbates, sugar fatty acid esters and addition products of ethylene oxide with sugar fatty acid esters, fatty acid alkanol amides of general formula (II)

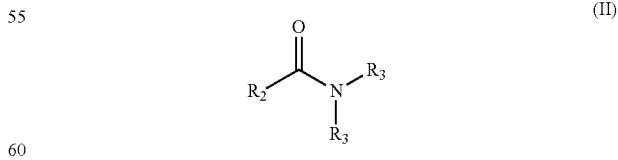

(II)

in which $R_2$ preferably means a linear or branched, saturated or unsaturated alkyl or alkenyl group having 8 to 24 carbon atoms and the groups $R_3$ stand for hydrogen or for the group—$(CH_2)_n OH$, in which n stands for the numbers 2 or 3, with the provision that at least one of the groups R3 stands for the aforementioned group —$(CH_2)_n OH$, addition products of ethylene oxide with fatty amines and/or alkyl oligo glucosides, in particular alkyl oligo glucosides based on hardened $C_{12/14}$ coconut alcohol having a DP of from about 1 to about 3, as are commercially obtainable for example under the INCI names "Coco Glucoside", "Decyl Glucoside" and/or "Lauryl Glucoside".

The optical and haptic properties of the cosmetic agents as contemplated herein can be increased yet further still if hair nourishing agents are added to them. Suitable further hair nourishing agents can be considered preferably to be cosmetically suitable oil, fat and/or wax components and/or vitamins.

Cosmetically suitable oil, wax and/or fat components can be selected preferably from mineral, natural and synthetic oil components and/or fatty substances.

Triglycerides and mixtures of triglycerides are usually used as natural (plant) oils. Preferred natural oils are coconut oil, (sweet) almond oil, walnut oil, peach kernel oil, apricot kernel oil, avocado oil, tea tree oil, soybean oil, sesame oil, sunflower oil, tsubaki oil, evening primrose oil, rice bran oil, palm kernel oil, mango kernel oil, lady's smock oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil, cocoa butter and Shea butter.

In particular, petroleum oils, paraffin oils and isoparaffin oils and synthetic hydrocarbons are used as mineral oils. An example of a hydrocarbon that can be used is, for example, the commercially available product 1,3-di-(2-ethylhexyl)-cyclohexane (Cetiol® S).

A dialkyl ether can also be used as oil component. Dialkyl ethers that can be used are in particular di-n-alkyl ethers having a total of between 12 and 36 carbon atoms, in particular 12 to 24 carbon atoms, such as di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether and also di-tert-butyl ether, di-isopentyl ether, di-3-ethyl decyl ether, tert-butyl-n-octyl ether, iso-pentyl-n-octyl ether and 2-methylpentyl-n-octyl ether. The di-n-octyl ether commercially available under the name Cetiol® OE is particularly preferably used as contemplated herein.

Silicone compounds are considered with preference as synthetic oils. Silicones provide excellent conditioning properties when applied to hair. In particular, they have a positive effect on the feel of the hair and the softness of the hair. It is therefore preferred to use silicones in the cosmetic agents as contemplated herein. Suitable silicones are preferably selected from the group of:
(i) polyalkyl siloxanes, polyaryl siloxanes, polyalkylaryl siloxanes, which are volatile or not volatile, straight-chained, branched or cyclic, cross-linked or non-cross-linked;
(ii) polysiloxanes which in their general structure contain one or more organofunctional groups selected from
(a) substituted or unsubstituted aminated groups;
(b) (per)fluorinated groups;
(c) thiol groups;
(d) carboxylate groups;
(e) hydroxylated groups;
(f) alkoxylated groups;
(g) acyloxyalkyl groups;
(h) amphoteric groups;
(i) bisulfite groups;
(j) hydroxyacylamino groups;
(k) carboxy groups;
(l) sulfonic acid groups; and
(m) sulfate or thiosulfate groups;
(iii) linear polysiloxane (A)-polyoxyalkylene (B) block copolymers of the type $(A-B)_n$ with n>3;
(iv) grafted silicone polymers with non-silicone-containing, organic parent structure which consist of an organic main chain formed from organic monomers containing no silicone, onto which at least one polysiloxane macromer has been grafted in the chain and also optionally at least at one chain end;
(v) grafted silicone polymers with polysiloxane parent structure, onto which non-silicone-containing organic monomers have been grafted, which comprise a polysiloxane main chain onto which at least one organic macromer containing no silicone has been grafted in the chain and optionally at least at one of the ends thereof; or
(vi) mixtures thereof.

In order to increase the hair shine and in order to attain a softer feel of the hair, it has proven to be particularly preferred if the cosmetic agents as contemplated herein contain at least one silicone. Cosmetic agents that are preferred as contemplated herein are therefore characterized in that they additionally contain at least one silicone in a total amount of from about 0.01 to about 3 wt. %, in relation to the total weight of the cosmetic agent.

In this context, cosmetic agents as contemplated herein that are preferred are those which contain—in relation to the total weight of the cosmetic agents as contemplated herein
from about 0.001 to about 10 wt. % of at least one protein which has a content of glutamic acid and/or aspartic acid of from about 10 to about 60%, preferentially from about 20 to about 60%, preferably from about 30 to about 60%, in particular from about 40 to about 60% in relation to the total content of all amino acids of the protein, and
calcium lactate and/or aluminium salts of formula MAl$(SO4)_2$, in which M stands for a potassium ion, in a total amount of from about 0.01 to about 10 wt. %,
from about 0.01 to about 3 wt. % of at least one silicone, wherein the cosmetic agent has a pH value, measured at 20° C., of from about pH 4.0 to about pH 5.0, preferably from about pH 4.1 to about pH 4.9, preferably from about pH 4.2 to about pH 4.8, in particular from about pH 4.3 to about pH 4.7.

Fatty substances are understood to mean fatty acids, fatty alcohols and also natural and synthetic waxes, which can be present either in solid form or in liquid form in aqueous dispersion.

Linear and/or branched, saturated and/or unsaturated fatty acids having 6 to 30 carbon atoms can be used as fatty acids. Fatty acids having 10 to 22 carbon atoms are preferred. Examples include the isostearic acids, such as the commercial products Emersol® 871 and Emersol® 875, and iso-palmitic acids such as the commercial product Edenor® IP 95, and also all further fatty acids sold under the commercial names Edenor® (Cognis). Further typical examples of such fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof.

The fatty acid cuts obtainable from coconut oil or palm oil are usually particularly preferred; the use of stearic acid is generally preferred in particular.

Saturated, mono- or polyunsaturated, branched or unbranched fatty alcohols having $C_6$ to $C_{30}$, preferably $C_{10}$ to $C_{22}$, and very particularly preferably $C_{12}$ to $C_{22}$ carbon atoms can be used as fatty alcohols. For example, decanol, octanol, octenol, dodecenol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, capryl alcohol, caprin alcohol, linoleyl alcohol, linolenyl alcohol and behenyl alcohol, and the guerbet alcohols thereof can be used, wherein this list is intended to be exemplary and non-limiting. The fatty alcohols, however, preferably originate from natural fatty acids, wherein recovery from the esters of fatty acids by reduction can usually be assumed. Fatty alcohol cuts which are produced by reduction of naturally occurring triglycerides, such as beef tallow, palm oil, peanut oil, rapeseed oil, cottonseed oil, soybean oil, sunflower oil and linseed oil, or fatty acid esters formed from the transesterification products thereof with corresponding alcohols and which therefore represent a mixture of different fatty alcohols can also be used as contemplated herein. Such substances can be purchased for example under the names Stenol®, for example Stenol® 1618, or Lanette®, for example Lanette® O, or Lorol®, for example Lorol® C8, Lorol® C14, Lorol® C18, Lorol® C8-18, HD-Ocenol®, Crodacol®, for example Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Of course, lanolin alcohols can also be used as contemplated herein, as can be purchased for example under the names Corona®, White Swan®, Coronet® or Fluilan®.

Solid paraffins or isoparaffins, carnauba wax, beeswax, candelilla wax, ozokerite, ceresin, spermaceti, sunflower wax, fruit wax, such as apple wax or citrus wax, and microwax from PE or PP can be used as natural or synthetic waxes. Such waxes are obtainable for example from the company Kahl & Co., Trittau.

Further fatty substances are, for example ester oils, i.e. the esters of $C_6$ to $C_{30}$ fatty acids having $C_2$ to $C_{30}$ fatty alcohols. The monoesters of fatty acids with alcohols having 2 to 24 carbon atoms are preferred. Examples of used fatty acid components in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof.

Examples of the fatty alcohol components in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachyl alcohol, gadoleyl alcohol, behenyl alcohol, erucyl alcohol and brassidyl alcohol and technical mixtures thereof. Particularly preferred are isopropyl myristate (Rilanit® IPM), isononanoic acid $C_{16}$-$C_{18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), and oleic acid decyl ester (Cetiol® V).

Dicarboxylic acid esters such as di-n-butyl adipate, di-(2-ethylhexyl) adipate, di-(2-ethylhexyl) succinate and di-isotridecyl acelaat, as well as diol esters such as ethylene glycol dioleate, ethylene glycol diisotridecanoate, propylene glycol di-(2-ethylhexanoate), propylene glycol diisostearate, propylene glycol dipelargonate, butanediol diisostearate, and neopentyl glycol dicaprylate, symmetrical, asymmetrical or cyclic esters of carbonic acid with fatty alcohols, glycerol carbonate or dicaprylyl carbonate (Cetiol® CC), ethoxylated or non-ethoxylated mono-, di-, and tri-fatty acid esters of saturated and/or unsaturated linear and/or branched fatty acids with glycerol, such as Monomuls® 90-O18, Monomuls® 90-L12, Cetiol® HE or Cutina® MD.

In order to increase the nourishing properties, the cosmetic agents as contemplated herein can contain at least one cationic polymer. Suitable cationic polymers are understood as contemplated herein to mean polymers which have "temporarily cationic" or "permanently cationic" groups in the main and/or side chain. As contemplated herein, "permanently cationic" polymers are those which comprise a cationic group irrespective of the pH value of the agent. These are generally polymers which contain a quaternary nitrogen atom, for example in the form of an ammonium group.

Suitable cationic polymers are, for example:

quaternized cellulose derivatives, especially Polyquaternium-10, as are commercially available for example under the names Celquat® and Polymer JR®, hydrophobically modified cellulose derivatives, for example the cationic polymers sold under the trade name SoftCat®, cationic alkyl polyglycosides, cationized honey, for example the commercial product Honeyquat® 50, cationic guar derivatives, such as in particular the products sold under the trade names Cosmedia®Guar N-Hance® and Jaguar®, polymeric dimethyl diallyl ammonium salts and copolymers thereof with esters and amides of acrylic acid and methacrylic acid, especially Polyquaternium-6 and Polyquaternium-7. The products commercially available under the names Merquat® 100 (poly(dimethyl diallyl ammonium chloride)) and Merquat® 550 (dimethyl diallyl ammonium chloride-acrylamide copolymer) are examples of such cationic polymers, copolymers of vinylpyrrolidone with quaternized derivatives of dialkylamino alkyl acrylate and methacrylate, such as vinylpyrrolidone-dimethylaminoethyl methacrylate copolymers quaternized with diethyl sulfate. Such compounds are commercially obtainable under the names Gafquat® 734 and Gafquat® 755, vinylpyrrolidone-vinylimidazolium methochloride copolymers, as are sold under the names Luviquat® FC 370, FC 550, FC 905 and HM 552, quaternized polyvinyl alcohol, and the polymers known under the names Polyquaternium 2, Polyquaternium 17, Polyquaternium 18, Polyquaternium-24, Polyquaternium 27, Polyquatemium-32, Polyquaternium-37, Polyquaternium 74 and Polyquaternium 89.

Particularly preferred cationic polymers are quaternized cellulose polymers, hydrophobically modified quaternized cellulose polymers, cationic guar derivatives and/or cationic polymers based on acrylic acid (derivative), particularly preferably selected from the polymers known under the INCI names Guar Hydroxypropyltrimonium Chloride, Polyquaternium-6, Polyquaternium-7, Polyquaternium-10, Polyquaternium-37 and/or Polyquaternium-67.

Very particularly preferred cationic polymers for the cosmetic agents as contemplated herein have proven to be cationic polysaccharide polymers, in particular quaternized cellulose polymers.

In order to ensure a satisfactory nourishing effect, the cosmetic agent as contemplated herein preferably additionally contains at least one cationic polymer in a total amount of from about 0.01 to about 3 wt. %, in relation to the total weight of the cosmetic agent.

In this context, cosmetic agents as contemplated herein that are preferred are those which contain—in relation to the total weight of the cosmetic agents as contemplated herein from about 0.001 to about 10 wt. % of at least one protein which has a content of glutamic acid and/or aspartic acid of from about 10 to about 60%, preferentially from about 20 to about 60%, preferably from about 30 to about 60%, in particular from about 40 to about 60% in relation to the total content of all amino acids of the protein, calcium lactate and/or aluminium salts of formula MAl $(SO4)_2$, in which M stands for a potassium ion, in a total amount of from about 0.01 to about 10 wt. %, and from about 0.01 to about 3 wt. % of at least one cationic polymer, selected from the group of cationic polysaccharides, wherein the cosmetic agent has a pH value, measured at 20° C., of from about pH 4.0 to about pH 5.0, preferentially from about pH 4.1 to about pH 4.9, preferably from about pH 4.2 to about pH 4.8, in particular from about pH 4.3 to about pH 4.7.

Suitable vitamins are preferably understood to mean the following vitamins, pro-vitamins and vitamin precursors and derivatives thereof:

vitamin A, for example retinol (vitamin $A_1$) and 3,4-didehydroretinol (vitamin $A_2$), β-carotin, vitamin A acid and esters thereof, vitamin A aldehyde, and vitamin A alcohol as well as esters thereof, vitamin B, such as vitamin $B_1$ (thiamin), vitamin $B_2$ (riboflavin), vitamin $B_3$ (nicotinic acid or nicotinic acid amide (niacinamide)), vitamin $B_5$ (pantothenic acid and panthenol) and derivatives thereof, in particular the esters and ethers of panthenol, pantolactone, and also cationically derivatised panthenols, vitamin $B_6$ (pyridoxine and also pyridoxamine and pyridoxal), vitamin C (ascorbic acid), in particular in the form of the palmitic acid ester, the glucosides, or phosphates, vitamin E (tocopherols, in particular α-tocopherol), vitamin F, such as linoleic acid, linolenic acid and arachidonic acid, and vitamin H ((3aS,4S, 6aR)-2-oxohexahydrothienol[3,4-d]-imidazol-4-valeric acid or biotin).

Vitamins, pro-vitamins and vitamin precursors from groups A, B, E and H are particularly preferred. Nicotinic acid amide, biotin, pantolactone and/or panthenol are very particularly preferred. Panthenol is preferred in particular.

The vitamin(s), vitamin derivative(s) and/or vitamin precursor(s) is/are used in the cosmetic agents as contemplated herein preferably in a total amount of from about 0.001 to about 2 wt. %, preferably from about 0.005 to about 1 wt. %, in particular from about 0.01 to about 0.5 wt. %, in relation to the total weight of the cosmetic agent.

Besides the components that are necessary as contemplated herein and the further above-mentioned preferred components, all further components known to a person skilled in the art for cosmetic compositions of this type can be used in principle.

Further active substances, auxiliaries and additives include, for example:

thickening agents such as gelatins or plant gums, for example agar-agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives such as amylose, amylopectin and dextrins, or fully synthetic hydrocolloids such as polyvinyl alcohol, structuring agents such as maleic acid and lactic acid, solvents and solubilisers, such as ethanol, isopropanol, ethylene glycol, propylene glycol, glycerol and diethylene glycol, active substances that improve the fibre structure, in particular mono-, di- and oligosaccharides, such as glucose, galactose, fructose, fruit sugar and lactose, dyes to color the agent, further substances to adjust the pH value, such as α- and β-hydroxycarboxylic acids, active substances such as allantoin and bisabolol, ceramides. Ceramides are understood to be N-acyl sphingosine (fatty acid amides of sphingosine) or synthetic analogues of such lipids (known as pseudoceramides), opacifiers, such as latex, styrene/PVP and styrene/acrylamide copolymers, pearlescent agents, such as ethylene glycol mono- and distearate, and PEG-3 distearate, pigments, propellants such as propane-butane mixtures, $N_2O$, dimethyl ether, $CO_2$ and air, viscosity adjusters such as salts (NaCl).

A further subject of the present disclosure relates to a method for maintaining the color of dyed keratin fibers, in which a cosmetic agent as contemplated herein is applied to the keratin fibers, once these have been dyed, within a period of time of from about 5 seconds to about 24 hours and is rinsed out from the keratin fibers as necessary after a reaction time of from about 30 seconds to about 30 minutes.

In this context, maintaining the color is understood to mean protecting the original color of the dyed keratin fibers. In particular, a color shift towards yellowish or bluish tones when cleaning or caring for the keratin fibers is to be avoided.

The term "coloring" within the scope of the present disclosure is also understood to mean artificially changing the color of the hair, in particular with use of oxidation dyes or temporary colorants.

In preferred methods as contemplated herein the cosmetic agents are applied within a shorter time following the coloring. Methods that are preferred as contemplated herein are therefore characterized in that the cosmetic agent is applied to the keratin fibers within a period of time of from about 5 seconds to about 20 hours, preferably from about 10 seconds to about 16 hours, preferably from about 30 seconds to about 14 hours, in particular from about 1 minute to about 12 hours, following the coloring.

That which has been said in relation to the cosmetic agents as contemplated herein applies, mutatis mutandis, with regard to further embodiments of the method as contemplated herein and also with regard to the cosmetic agents used in the method as contemplated herein.

Lastly, a further subject of the present disclosure is the use of a combination of a) from about 0.001 to about 10 wt. % of at least one protein which has a content of glutamic acid and/or aspartic acid of from about 10 to about 60%, in relation to the total content of all amino acids of the protein, and b) from about 0.01 to about 10 wt. % of at least one salt which comprises at least one divalent cation, and/or of at least one salt which comprises at least one trivalent cation to maintain the color of dyed keratin fibers.

By using the aforementioned combination of an acid protein and at least one salt, the loss of color that occurs when cleaning and/or caring for dyed keratin fibers can be avoided. In addition, by using the aforementioned combination, the color shift that occurs when cleaning and/or caring for dyed keratin fibers is also reduced. In this way, the color attained after coloring the hair is maintained, unchanged, for longer.

That which has been said in relation to the cosmetic agents as contemplated herein and in relation to the method as contemplated herein applies, mutatis mutandis, with regard to further embodiments of the use as contemplated herein.

The present disclosure is outlined in particular by the following points:

1. A cosmetic agent for treating keratin fibers, said agent containing in a cosmetically acceptable carrier—in relation to the total weight of the cosmetic agent
   a) from about 0.001 to about 10 wt. % of at least one protein which has a content of glutamic acid and/or aspartic acid of from about 10 to about 60%, in relation to the total content of all amino acids of the protein, and
   b) from about 0.01 to about 10 wt. % of at least one salt which comprises at least one divalent cation, and/or of at least one salt which comprises at least one trivalent cation.

2. The cosmetic agent according to point 1, characterized in that the at least one protein has a content of glutamic acid and/or aspartic acid of from about 20 to about 60%, preferably from about 30 to about 60%, in particular from about 40 to about 60%, in relation to the total content of all amino acids of the protein.

3. The cosmetic agent according to any one of points 1 or 2, characterized in that the at least one protein has a $pK_s$, value of from about 3.5 to about 6.5, preferably from about 4.0 to about 6.0, preferably from about 4.5 to about 6.0, in particular from about 4.5 to about 5.5.

4. The cosmetic agent according to any one of the preceding points, characterized in that a 1 wt. % solution of the at least one protein, in relation to the total weight of the solution, has a pH value, measured at 20° C., of from about pH 3.5 to about pH 7.0, preferably from about pH 3.5 to about pH 6.0, in particular from about pH 3.5 to about pH 5.2.

5. The cosmetic agent according to any one of the preceding points, characterized in that the at least one protein has a mean molecular weight $M_w$ of from about 100 to about 5,000 Da, preferably from about 100 to about 4,000 Da, preferably from about 200 to about 3,000 Da, in particular from about 300 to about 1,200 Da.

6. The cosmetic agent according to any one of the preceding points, characterized in that the at least one protein contains from about 2 to about 40 amino acids, preferentially from about 2 to about 30 amino acids, preferably from about 2 to about 25 amino acids, in particular from about 2 to about 18 amino acids.

7. The cosmetic agent according to any one of the preceding claims, characterized in that the at least one protein is contained in a total amount of from about 0.001 to about 8 wt. %, preferably from about 0.01 to about 5 wt. %, preferably from about 0.1 to about 3 wt. %, in particular from about 0.3 to about 2 wt. %, in relation to the total weight of the cosmetic agent.

8. The cosmetic agent according to any one of the preceding points, characterized in that what is contained as salt which comprises at least one divalent cation is a salt of lactic acid, selected from the group of magnesium salts, calcium salts, copper salts, zinc salts, iron(II) salts and mixtures of these salts, in particular calcium salts of lactic acid.

9. The cosmetic agent according to any one of the preceding points, characterized in that the salt comprising at least one divalent cation is contained in a total amount of from about 0.01 to about 8 wt. %, preferentially from about 0.1 to about 5 wt. %, preferably from about 0.2 to about 3 wt. %, in particular from about 0.3 to about 2 wt. %, in relation to the total weight of the cosmetic agent.

10. The cosmetic agent according to any one of the preceding claims, characterized in that what is contained as salt which comprises at least one trivalent cation is a salt from the group of titanium salts, zirconium salts, gallium salts, aluminum salts, in particular aluminum salts of formula $MAl(SO_4)_2$, in which M stands for a potassium, sodium, guanidinium or ammonium ion.

11. The cosmetic agent according to any one of the preceding claims, characterized in that the salt which comprises at least one trivalent cation is contained in a total amount of from about 0.01 to about 5 wt. %, preferably from about 0.05 to about 4.5 wt. %, preferably from about 0.1 to about 4.0 wt. %, more preferably from about 0.15 to about 3.5 wt. %, even more preferably from about 0.5 to about 3.0 wt. %, in particular from about 0.8 to about 2.5 wt. %, in relation to the total weight of the cosmetic agent.

12. The cosmetic agent according to any one of the preceding claims, characterized in that the cosmetic agent has a pH value, measured at 20° C., of from about pH 4.0 to about pH 5.0, preferentially from about pH 4.1 to about pH 4.9, preferably from about pH 4.2 to about pH 4.8, in particular from about pH 4.3 to about pH 4.7.

13. The cosmetic agent according to any one of the preceding points, characterized in that the cosmetic agent additionally contains at least one cationic polymer in a total amount of from about 0.01 to about 3 wt. %, in relation to the total weight of the cosmetic agent.

14. A method for maintaining the color of dyed keratin fibers, in which a cosmetic agent according to any one of points 1 to 13 is applied to the keratin fibers, once these have been dyed, within a period of time of from about 5 seconds to about 24 hours and is rinsed out from the keratin fibers as necessary after a reaction time of from about 30 seconds to about 30 minutes.

15. Use of a combination of
    a) from about 0.001 to about 10 wt. % of at least one protein which has a content of glutamic acid and/or aspartic acid of from about 10 to about 60%, in relation to the total content of all amino acids of the protein, and
    b) from about 0.01 to about 10 wt. % of at least one salt which comprises at least one divalent cation, and/or of at least one salt which comprises at least one trivalent cation to maintain the color of dyed keratin fibers.

The following examples are intended to explain preferred embodiments of the invention, but without limiting the invention thereto.

EXAMPLES

The following cosmetic agents as contemplated herein were produced (the specified amounts relate here to amounts in wt. %):

a) Color-protect shampoos

|  | E1 | E2 | E3 | E4 |
|---|---|---|---|---|
| Sodium Laureth Sulfate | 11.00 | 11.00 | 11.00 | 11.00 |
| Cocamidopropyl Betaine | 1.00 | 1.50 | 1.50 | 1.50 |
| Disodium Cocoamphodiacetate | 0.50 | — | — | — |
| Cocamide MEA | 0.50 | 0.50 | 0.50 | 0.50 |
| PEG-12 Dimethicone | 0.50 | 0.30 | 0.30 | 0.30 |
| Glycol Distearate | 1.20 | — | — | — |
| PEG-7 Glyceryl Cocoate | 0.40 | 0.60 | 0.60 | 0.60 |
| Polyquaternium-10 | 0.90 | 0.60 | 0.60 | 0.60 |
| Panthenol | 0.30 | 0.20 | 0.20 | 0.20 |
| Apricot Kernel Oil | 0.05 | — | — | — |
| Hydrogenated Castor Oil | 0.20 | 0.10 | 0.10 | 0.10 |
| Protein with at least 10 to 60% aspartic acid and/or glutamic acid | 0.5 | 1.0 | 1.0 | 1.0 |
| Calcium Lactate | 0.2 | 0.5 | — | 0.2 |
| KAl(SO$_4$)$_2$ | — | — | 1.0 | 0.8 |
| Preservatives, Perfume, possibly Acidifer | q.s. | q.s. | q.s. | q.s. |
| Water | to 100 | to 100 | to 100 | to 100 |
| pH | 4.5 | 4.4 | 4.4 | 4.4 |

The shampoos E1 to E4 were applied to wet, dyed hair and were rinsed out with water after being left to take effect for approximately one minute. The hair, after having been cleaned, had a brilliant hair color, which had not changed. In addition, the hair had a visually appealing shine and felt soft.

b) Conditioners

|  | E4 | E5 | E6 | E7 |
|---|---|---|---|---|
| Cetearyl Alcohol | 2.50 | 2.50 | 2.50 | 2.50 |
| Quaternium-87 | 2.00 | 2.00 | 2.00 | 2.00 |
| Propylene Glycol | 0.50 | 0.50 | 0.50 | 0.50 |
| Isopropyl Myristate | 0.30 | 0.30 | 0.30 | 0.30 |
| Distearoylethyl Hydroxyethylmonium Methosulfate | 0.50 | 0.50 | 0.50 | 0.50 |
| Calcium Hydroxide | 0.54 | — | — | — |
| Phenoxyethanol | 0.40 | 0.40 | 0.40 | 0.40 |
| Stearamidopropyl Dimethylamine | 0.30 | 0.30 | 0.30 | 0.30 |
| Perfume | 0.25 | 0.25 | 0.25 | 0.25 |
| Sodium Methylparaben | 0.20 | 0.20 | 0.20 | 0.20 |
| Polyquaternium-37 | 0.20 | 0.20 | 0.20 | 0.20 |
| Dicaprylyl Carbonate | 0.20 | 0.20 | 0.20 | 0.20 |
| Panthenol | 0.10 | 0.10 | 0.10 | 0.10 |
| Benzophenone-4 | 0.05 | 0.05 | 0.05 | 0.05 |
| Amidodimethicone/ Morpholinomethyl Silsesquioxane Copolymer | 0.02 | 0.02 | 0.02 | 0.02 |
| Glycerol | 0.01 | 0.01 | 0.01 | 0.01 |
| Hydrolysed Keratin | 0.01 | 0.01 | 0.01 | 0.01 |
| Protein with at lest 10 to 60% aspartic acid and/or glutamic acid | 0.5 | 1.0 | 1.0 | 1.0 |
| Calcium Lactate | 0.2 | 0.5 | — | 0.2 |
| KAl(SO$_4$)$_2$ | — | — | 1.0 | 0.8 |
| Preservatives, Perfume, possibly Acidifer | q.s. | q.s. | q.s. | q.s. |
| Water | to 100 | to 100 | to 100 | to 100 |
| pH | 4.3 | 4.3 | 4.3 | 4.3 |

The conditioners E4 to E7 were applied to wet, dyed hair and were rinsed out with water after being left to take effect for approximately one minute. The hair, after having been cleaned, had a brilliant hair color, which had not changed. In addition, the hair had a visually appealing shine and felt soft.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A color-protect shampoo having a pH of 4.4 to 4.5 measured at 20° C., utilized to maintain the color of dyed keratin fibers, and consisting of:
    sodium laureth sulfate present in an amount of 11 weight percent in relation to the total weight of the shampoo;
    cocamidopropyl betaine present in an amount of 1 to 1.5 weight percent in relation to the total weight of the shampoo;
    disodium cocoamphodiacetate present in an amount of 0 to 0.5 weight percent in relation to the total weight of the shampoo;
    cocamide MEA present in an amount of 0.5 weight percent in relation to the total weight of the shampoo;
    PEG-12 dimethicone present in an amount of 0.3 to 0.5 weight percent in relation to the total weight of the shampoo;
    glycol distearate present in an amount of 0 to 1.2 weight percent in relation to the total weight of the shampoo;
    PEG-7 glyceryl cocoate present in an amount of 0.4 to 0.6 weight percent in relation to the total weight of the shampoo;
    polyquaternium-10 present in an amount of 0.6 to 0.9 weight percent in relation to the total weight of the shampoo;
    panthenol present in an amount of 0.2 to 0.3 weight percent in relation to the total weight of the shampoo;
    apricot kernel oil present in an amount of 0 to 0.05 weight percent in relation to the total weight of the shampoo;
    hydrogenated castor oil present in an amount of 0.1 to 0.2 weight percent in relation to the total weight of the shampoo;
    a protein with at least a 10 to 60% content of aspartic acid and/or glutamic acid in relation to the total content of all amino acids of the protein and present in an amount of 0.5 to 1 weight percent in relation to the total weight of the shampoo;
    calcium lactate present in an amount of 0 to 0.5 weight percent in relation to the total weight of the shampoo;
    KAl(SO$_4$)$_2$ present in an amount of 0 to 1 weight percent in relation to the total weight of the shampoo;
    preservatives, perfume, and optionally an acidifer; and
    water present in an amount such that a total weight of the shampoo is 100 wt %.

2. The shampoo according to claim 1, wherein the protein has a content of glutamic acid and/or aspartic acid of about 30 to about 60% in relation to the total content of all amino acids of the protein.

3. The shampoo according to claim 2, wherein the protein has a pKs value of about 3.5 to about 6.5.

4. The shampoo according to claim 3, wherein the protein has a mean molecular weight Mw of about 100 to about 5,000 Da and comprises about 2 to about 40 amino acids.

5. The shampoo according to claim 1, wherein the protein has a content of glutamic acid and/or aspartic acid of about 40 to about 60% in relation to the total content of all amino acids of the protein.

6. The shampoo according to claim 5, wherein the protein has a pKs value of about 3.5 to about 6.5.

7. The shampoo according to claim 6, wherein the protein has a mean molecular weight Mw of about 300 to about 1,200 Da, and wherein the protein contains 2 to 18 amino acids.

8. The shampoo according to claim 6, wherein the protein has a mean molecular weight Mw of about 100 to about 5,000 Da.

9. The shampoo according to claim 8, wherein the protein comprises about 2 to about 40 amino acids.

10. The shampoo according to claim 1, wherein the protein has a mean molecular weight Mw of about 300 to about 1,200 Da, and wherein the protein contains 2 to 18 amino acids.

11. A conditioner having a pH of about 4.3 measured at 20° C., utilized to maintain the color of dyed keratin fibers, and consisting of:
cetearyl alcohol present in an amount of 2.5 weight percent in relation to the total weight of the conditioner;
quaternium-87 present in an amount of 2 weight percent in relation to the total weight of the conditioner;
propylene glycol present in an amount of 0.5 weight percent in relation to the total weight of the conditioner;
isopropyl myristate present in an amount of 0.3 weight percent in relation to the total weight of the conditioner;
distearoylethyl hydroxyethylmonium methosulfate present in an amount of 0.5 weight percent in relation to the total weight of the conditioner;
calcium hydroxide present in an amount of 0 to 0.54 weight percent in relation to the total weight of the conditioner;
phenoxyethanol present in an amount of 0.4 weight percent in relation to the total weight of the conditioner;
stearamidopropyl dimethylamine present in an amount of 0.3 weight percent in relation to the total weight of the conditioner;
perfume present in an amount of 0.25 weight percent in relation to the total weight of the conditioner;
sodium methylparaben present in an amount of 0.2 weight percent in relation to the total weight of the conditioner;
polyquaternium-37 present in an amount of 0.2 weight percent in relation to the total weight of the conditioner;
dicaprylyl carbonate present in an amount of 0.2 weight percent in relation to the total weight of the conditioner;
panthenol present in an amount of 0.1 weight percent in relation to the total weight of the conditioner;
benzophenone-4 present in an amount of 0.05 weight percent in relation to the total weight of the conditioner;
amidodimethicone/morpholinomethyl silsesquioxane copolymer present in an amount of 0.02 weight percent in relation to the total weight of the conditioner;
glycerol present in an amount of 0.01 weight percent in relation to the total weight of the conditioner;
hydrolysed keratin present in an amount of 0.01 weight percent in relation to the total weight of the conditioner;
a protein with at least a 10 to 60% content of aspartic acid and/or glutamic acid in relation to the total content of all amino acids of the protein and present in an amount of 0.5 to 1 weight percent in relation to the total weight of the conditioner;
calcium lactate present in an amount of 0 to 0.5 weight percent in relation to the total weight of the conditioner;
$KAl(SO_4)_2$ present in an amount of 0 to 1 weight percent in relation to the total weight of the conditioner;
preservatives and optionally an acidifer; and
water present in an amount such that a total weight of the conditioner is 100 wt %.

12. The conditioner according to claim 11, wherein the protein has a content of glutamic acid and/or aspartic acid of about 30 to about 60% in relation to the total content of all amino acids of the protein.

13. The conditioner according to claim 12, wherein the protein has a pKs value of about 3.5 to about 6.5.

14. The conditioner according to claim 13, wherein the protein has a mean molecular weight Mw of about 100 to about 5,000 Da and comprises about 2 to about 40 amino acids.

15. The conditioner according to claim 11, wherein the protein has a content of glutamic acid and/or aspartic acid of about 40 to about 60% in relation to the total content of all amino acids of the protein.

16. The conditioner according to claim 15, wherein the protein has a pKs value of about 3.5 to about 6.5.

17. The conditioner according to claim 16, wherein the protein has a mean molecular weight Mw of about 300 to about 1,200 Da, and wherein the protein contains 2 to 18 amino acids.

18. The conditioner according to claim 16, wherein the protein has a mean molecular weight Mw of about 100 to about 5,000 Da.

19. The conditioner according to claim 18, wherein the protein comprises about 2 to about 40 amino acids.

20. A method for maintaining the color of dyed keratin fibers, the method comprising:
applying the shampoo according to claim 1 to the keratin fibers, wherein the keratin fibers have been dyed within a period of 5 seconds to 24 hours; and
rinsing the shampoo out from the keratin fibers after a reaction time of 30 seconds to 30 minutes.

* * * * *